(12) United States Patent
Kamei et al.

(10) Patent No.: US 6,300,100 B1
(45) Date of Patent: Oct. 9, 2001

(54) PROCESS FOR PREPARING TISSUE FACTOR PATHWAY INHIBITOR

(75) Inventors: Shintaro Kamei; Yuichi Kamikubo; Tsutomu Hamuro, all of Kumamoto (JP)

(73) Assignee: Juridical Foundation the Chemo-Sero-Therapeutic Research Institute, Kumamoto-ken (JP)

( * ) Notice: Subject to any disclaimer, the term of this patent is extended or adjusted under 35 U.S.C. 154(b) by 0 days.

(21) Appl. No.: 08/266,542

(22) Filed: Jun. 28, 1994

(30) Foreign Application Priority Data

Jun. 30, 1993 (JP) .................................................... 5-188746

(51) Int. Cl.[7] ........................... C12N 15/09; C12P 21/06; C12P 21/04
(52) U.S. Cl. ...................... 435/69.2; 435/69.1; 435/70.1
(58) Field of Search .............................................. 435/69.2

(56) References Cited

U.S. PATENT DOCUMENTS 5,422,250 * 6/1995 Mignot et al. ....................... 435/69.6

OTHER PUBLICATIONS

Freifelder et al. Physical Biochemistry. New York; W.H. Freeman & Co., pp. 260–262, 1982.*

Wesselschmidt, R. et al. Blood 80, R63a, abstract 1043, 1992.*

Wun, T.–C. Blood 79, 430–438, 1992.*

* cited by examiner

*Primary Examiner*—Yvonne Eyler
(74) *Attorney, Agent, or Firm*—Foley & Lardner (57) ABSTRACT

In a process for preparing Tissue Factor Pathway Inhibitor (TFPI) by the genetically engineered technique by the use of a transformed animal cell wherein a DNA encoding human TFPI is introduced, the improvement which comprises culturing said transformed animal cell in a culture medium supplemented with a sulfated polysaccharide to protect an intact TFPI produced by said transformed animal cell from cleavage by proteases present in the culture medium.

4 Claims, 4 Drawing Sheets

PROCESS FOR PREPARING TISSUE FACTOR PATHWAY INHIBITOR

The present invention relates to a process for preparing blood coagulation inhibitor which has hitherto been known as Tissue Factor Inhibitor (TFI), Extrinsic Pathway Inhibitor (EPI) or Lipoprotein-associated Coagulation Inhibitor (LACI) and which has recently been given a unified name of Tissue Factor Pathway Inhibitor (hereinafter referred to as "TFPI"). More particularly, the present invention relates to a process for preparing an intact TFPI from a transformed animal cell wherein a DNA encoding a human TFPI is introduced.

PRIOR ART

Bleeding is one of the most serious lesions in the living body. There is a series of blood coagulation reactions for controlling the bleeding within the living body. These reactions are classified into two pathways, i.e. the intrinsic and extrinsic pathways. At present, for the initiation mechanism of a physiological coagulation reaction, the extrinsic pathway initiated by Tissue Factor (hereinafter referred to as "TF") is considered to be more important than the intrinsic pathway [Davie, E. W., Biochem., 30, p10363 (1991)]. In case of the extrinsic pathway, TF, which is considered normally not to contact with blood, becomes in contact with blood due to vascular damage or any other causes and then it is rapidly bound with the blood coagulation factor VII(a). The resulting TF-Factor VIIa complex activates the blood coagulation Factors IX and X, leading to proteolytical activation of prothrombin to thrombin. Finally, thrombin stimulates platelets and forms fibrin clot or thrombi.

In early studies as to the control of blood coagulation initiated by TF, it was suggested that serum shows an inhibitory activity against the tissue thromboplastin (the old name of TF) [Thomas L., Bull. Johns Hopkins Hosp. 81, p26 (1947)]. It was also shown that the inhibitory activity was dependent on the presence of calcium. Based on these facts, Hjort demonstrated that this serum inhibitor targeted the TF-factor VIIa complex and required calcium [Hjort, P. F., Scand. J. Clin. Lab. Invest. 9, p1 (1957)]. In 1980's, Sanders et al. showed that Factor X is necessary for the serum inhibitor [Sanders, N. L., Blood, 66, p204 (1985)] and a density gradient centrifugation of plasma also proved that it is present in a lipoprotein fraction. The serum inhibitor and its mechanism of inhibition have been mainly elucidated by Broze et al. who purified the inhibitor from established human liver (HepG2) cell [Broze Jr., G. J., Proc. Natl. Acad. Sci. U.S.A., 84, p1886 (1987)]. The cDNA encoding TFPI is cloned from human placental $\lambda$gt11 cDNA library by using anti-TFPI antibody. From this nucleotide sequence, a whole amino acid sequence was deduced and suggested the mechanism of inhibition [Wun, T C., J. Biol. Chem., 263, p6001 (1988)]. According to these data, TFPI consisted of 304 amino acids including a signal sequence of 28 amino acids and has three regions of amino acid sequence homologous to the Kunitz-type protease inhibitor. The Kunitz-type protease inhibitors were known to inhibit trypsin-like proteases, for example, soy bean trypsin inhibitor (SBTI) or aprotinin. In case of TFPI, it has been shown that, among the three Kunitz-type regions, the reaction site of the second Kunitz-type region is necessary for the inhibition of factor Xa whereas the reaction sites of the first and the second Kunitz-type regions are necessary for the inhibition of the TF-factor VIIa complex. TFPI binds and inhibits factor Xa directly and inhibits TF-factor VIIa activity in a factor Xa-dependent fashion in a reaction that appears to involve the formation of a Xa-TFPI-VIIa-TF quaternary complex. The reaction site of the third Kunitz-type region is shown to be unnecessary for the inhibition and the role of this reaction site still remains unknown [Girard, T. J., Nature, 338, p518 (1989)]. The N-terminal region of TFPI has a cluster of negatively charged (or acidic) amino acids, and the C-terminal region has a cluster of positively charged (or basic) amino acids which is important of inhibitory function.

TFPI is mainly produced in endothelial cells [Bajaj, M. S., Proc. Natl. Acad. Sci. USA, 87, p8869 (1990)] and is present at a concentration of about 100 ng/mL in plasma, among of which a percentage of TFPI free from lipoproteins is several % to several ten %. TFPI is also found in platelets in a quite small amount and is suggested to be bound with a heparin-like substance on endothelial cells of the blood vessel since TFPI was released into plasma when heparin was administered to healthy persons [Novotny, W. F., Blood, 78, p394 (1991)].

It was proved that TFPI in blood was bound with lipoproteins based on the fact that TFPI was found in a lipoprotein fraction even after a density gradient centrifugation or gel filtration thereof and the fact that TFPI purified from plasma was associated with apolipoprotein A-II under non-reducing conditions. It was also found that the lipoprotein-bound TFPI is dissociated under reducing conditions [Novotny, W. F., J. Biol. Chem., 264, p18832 (1989)]. However, the mechanism of TFPI binding with lipoproteins and the significance thereof is still unknown in detail. A concentration of lipoproteins in plasma greatly varies depending on a variety of conditions, and TFPI has been considered to be a very important factor for elucidating a relationship between the thrombus formation and the concentration of lipoproteins especially in a pathological condition such as arteriosclerosis. In recent years, it has also been studied to use TFPI as an agent for preventing reocclusion in an arteriosclerosis model [Haskel, E. J., Circulation, 84, p821 (1991)].

Since TFPI is present in blood only in a quite small amount, it has been prepared as a recombinant protein by a genetically engineering technique by many researchers. For example, it has been reported an expression of recombinant TFPI from mouse C127 cells [Day, K. C., Blood, 76, p1538 (1990)], BHK cells [Pederson, A. H., J. Biol. Chem., 265, p16786 (1990)], CHO cells, SK hepatoma cells [Wun, T C., Thromb. Haemost., 68, p54 (1992)] as a host cell. However, all of these recombinant TFPIs except for that from SK hepatoma cells were reported to apparently exhibit a lower specific activity than that of TFPI derived from plasma or TFPI on the endothelial cells of the blood vessel [Wesselschmidt, R., Blood, 79, p2004 (1992); Lindahl, A. K., Thromb. Res., 62, p607 (1991)]. This decrease in activity was mainly due to cleavage of the C-terminal basic region of the recombinant TFPI. It has been shown that the molecular species devoid of the C-terminal region is lowered in the binding activity to heparin, especially in the inhibitory efficiency to Factor Xa, and hence, the C-terminal region is physiologically very important. An intact molecular species with the C-terminal basic region and its truncated molecular species can be separated by heparin agarose chromatography or cation exchange chromatography with NaCl concentration gradient [Wesselschmidt, R., Blood, 79, p2004 (1992); Nordfang, O., Biochem., 30, p10371 (1991)], along with any purification steps, for example, affinity chromatography using an anti-TFPI antibody. A yield of the intact molecular species obtained from these cell cultures was at most 40%, normally 10% or less. The only exception is the case of using SK hepatoma cells as a host cell, which are known to produce intrinsically TFPI [Wun, T C., Thromb. Haemost., 68, p54 (1992)]. It was reported that the intact recombinant TFPI was obtained at almost 100% from the conditioned medium of the TFPI-expressing cells where an exogenous TFPI gene was introduced. These results show that, when cells other than those producing TFPI intrinsically were used as a host cell, it is very difficult to obtain the intact recombinant TFPI at a high yield. Accordingly, it has hitherto been very difficult to prepare the intact TFPI molecular species in a large amount by using animal cell strains such as CHO or BHK cells, which cells are known to be capable of producing TFPI in such a stable fashion and at such a high expression rate that is can be used at an industrial level.

SUMMARY OF THE INVENTION

The present inventors have intensively studied, and as a result, have found that a sulfated polysaccharide can effectively be used for protecting the intact TFPI expressed in a conditioned medium of a transformed animal cell from cleavage by proteases derived from host cell in culture medium. As mentioned above, the molecular species with the truncated C-terminal basic region shows a different behavior in the heparin agarose chromatography from that of the intact molecular species, and hence, it is estimated that the C-terminal region deeply participates in the binding with heparin. On the other hand, it is known that heparin, like the other sulfated polysaccharides, exhibits an anti-coagulation activity in plasma and this activity is amplified by the presence of TFPI [Wun, T C., Blood, 79, p430 (1992)]. Under the circumstances, the present inventors have found that the C-terminal basic region of TFPI is protected from the cleavage by proteases by adding a sulfated polysaccharide to the culture medium. According to the present invention, the intact TFPI can be obtained at a yield of at least 80% based on TFPI expressed in a culture medium even in an expression system employing as a host cell the animal cell from which intact TFPI has hitherto been obtained in quite low yield.

An object of the present invention is to provide in an improved process for preparing Tissue Factor Pathway Inhibitor (TFPI) by the genetically engineered technique using a transformed animal cell wherein the cDNA encoding human TFPI is introduced, which comprises culturing said transformed animal cell in a culture medium supplemented with a sulfated polysaccharide in order to protect the intact TFPI produced by said transformed animal cell from cleavage by proteases present in the culture medium.

This and other objects and advantages of the invention will be apparent to those skilled in the art from the following description.

DETAILED DESCRIPTION OF THE INVENTION

The sulfated polysaccharide used in the present invention includes, for example, heparin as mentioned above, a low molecular weight heparin, pentosan polysulfate, dextran sulfate, heparan sulfate, dermatan sulfate, and the like. An amount of the sulfated polysaccharide to be added to a culture medium may vary depending on an amount of recombinant TFPI expressed from a transformed cell, saving of costs, and a degree of a toxic effect on cells, but it is usually added at a concentration of 0.01 U/mL or more (converted into activity of heparin) per 1 μg/mL of TFPI (the specific activity of heparin is used herein as 140 U/mg based on the prescription of the Japan Pharmacopeia). As mentioned above, the present invention is characterized by adding the sulfated polysaccharide to a culture medium in the culture of a transformed animal cell to which TFPI expression gene is introduced. The present invention is explained in more detail by the following preferable embodiments.

For expression of the TFPI gene by the host cell and effective production of a recombinant TFPI, an efficient expression of a structural gene is desired. For this purpose, a promotor upstream from the TFPI structural gene to be introduced into the host cell should be selected from those with a high activity, including an SV40 early or late promotor, an adenovirus promotor, a cytomegalovirus promotor, a metallothionein promotor, and the like. The promotor used in the present invention is a chicken β actin promotor (Japanese Patent First Publication (Kokai) No. 2-5890). In addition, a variety of enhancer sequences are also used for increasing the promotor activity. The enhancer sequence may be a variety of sequences which function in eucaryotic cells, including an SV40 enhancer, a cytomegallovirus enhancer, a polyoma stem cell enhancer, and the like.

A preferable TFPI expression vector of the present invention comprises the TFPI structural gene and a polyadenylation signal downstream thereof under the control of an enhancer which functions in eucaryotic cells and the chicken β actin promotor, to which is further linked a gene sequence comprising a replication origin and a drug resistant gene.

A host cell where the above-mentioned TFPI expression vector is introduced may be any animal cell which can express recombinant TFPI, and is preferably an animal cell where a desired transformed cell can easily be separated, for example, a Chinese hamster ovary (CHO) cell.

The introduction of the gene fragment for transformation into the host cell can be conducted by known methods such as a calcium phosphate method, a DEAE-DEXTRAN method, a lipofectin method, an electroporation. In order to facilitate the selection of transformed cells, an animal cell which is deficient in a marker gene of said expression vector is used. For example, by using CHO cells which are deficient in a dihydrofolate reductase (DHFR) gene as a host cell, introducing an expression vector having the DHFR gene into said host cell, and culturing the host cell in a selection culture medium deficient in nucleoside, there can be selected the CHO cells wherein the DHFR gene is introduced and expressed and also the desired CHO cells wherein the TFPI gene will also be introduced. In addition, in case of the thus produced transformed cell, the TFPI gene can also be amplified, and as a result, there can be obtained a transformed cell which can produce TFPI in a large amount.

When an amplifiable gene such as the above-mentioned DHFR gene is used for selection, the TFPI gene which is introduced into the transformed cell together with the DHFR gene is also amplified by culturing the cells under conditions suitable for gene amplification, for example, in the presence of methotrexate in case of the DHFR gene. As a result, a produced amount of TFPI per cell is increased and a large amount of TFPI can be secreted into a culture medium. From these transformed cells, there can be selected those cells which secrete the recombinant TFPI into the culture medium more stably by a cloning procedure such as a limiting dilution method. This procedure can also be applicable to animal cells other than CHO cells, as is well known to a person skilled in the art.

The present invention is characteristic in the protection of TFPI secreted and accumulated in a culture medium from cleavage by a protease during culture of the cells with high expression of the recombinant TFPI obtained as mentioned above, and this protection can surely and simply be achieved by culturing said cells in a culture medium containing a sulfated polysaccharide. Thus, the transformed cells to be used in the present invention are not limited to those discussed herein above but any known transformant cells can be employed in the present invention. The sulfated polysaccharide should be used at a concentration which does not affect growth of the cells, and the amount thereof should be determined with consideration of an expression amount of the desired product and saving of costs. However, heparin, which is normally used for medical purpose as an anti-coagulating agent, is preferable, and is added at a final concentration of not less than 0.01 U/mL (0.07 µg/mL), preferably 0.1 to 20 U/mL, per 1 µg expressed TFPI/mL culture medium. Another sulfated polysaccharides can also be used in an amount corresponding to the above amount of heparin. The amount of the sulfated polysaccharides to be added to a culture medium can also be determined by the above-mentioned criteria, and is not less than 0.3 µg/mL of a final concentration in case of dextran sulfate and pentosan sulfate, and not less than 14 µg/mL of a final concentration in case of dermatan sulfate and heparan sulfate, per 1 µg/mL of TFPI concentration.

According to the present invention, almost all of the active TFPI contained in a culture medium can be collected as an intact TFPI by culturing the transformed cell with high expression of the recombinant TFPI in accordance with the above-mentioned procedure (i.e. in a culture medium supplemented with a sulfated polysaccharide). The TFPI protein produced and accumulated in the culture medium is directly concentrated after removal of the cells and then separated and purified by a suitable combination of known methods for separation, which include a method utilizing a difference in solubility such as a salting out and a solvent precipitation method; a method utilizing mainly a difference in a molecular weight such as dialysis, ultrafiltration, gel filtration and SDS-polyacrylamide gel electrophoresis; a method utilizing a difference in charge such as ion exchange chromatography; a method utilizing a specific affinity such as affinity chromatography; a method utilizing a difference in hydrophobicity such as reverse phase high performance liquid chromatography; a method utilizing a difference in isoelectric point such as isoelectrofocusing; and the like.

In a preferable embodiment, after the obtained culture medium is concentrated with ultrafiltration filter membrane, an antibody affinity chromatography is conducted to purify TFPI. From the eluted fraction of TFPI, the intact TFPI can be easily separated from the cleaved TFPI by heparin affinity chromatography or cation exchange chromatography. If necessary, the obtained solution containing the TFPI protein can be made into powder by lyophilization wherein a stabilizing agent such as a sugar (e.g. sorbitol, mannitol, dextrose, etc.), a sugar alcohol, an amino acid, glycerol, human serum albumin may also be added.

According to the present invention, the greater part of TFPI which is produced by the gene recombinant technique utilizing an animal cell as a host cell can be obtained stably as the intact TFPI in a large amount. Thus, the present invention can produce the intact recombinant TFPI in an amount sufficient for preparing a practically usable pharmaceutical preparation as the prophylaxis and treatment of thrombosis in various diseases with abnormality in the blood coagulation system, such as disseminated intravascular coagulation (DIC).

The present invention is explained in more detail by the following Examples but it should not be construed to be limited thereto.

EXAMPLE

Material and Evaluation:

(1) Reagents

Restriction enzymes and modification enzymes were purchased from Takara Shuzo, a dideoxy sequencing kit from Toyobo, fetal bovine serum, dialyzed fetal bovine serum and MEM alpha from Gibco-BRL, ASF culture medium 104 from Ajinomoto, Sodium n-butyrate, methotrexate, p-APMSF: p-amidinophenylmethanesulfonyl fluoride and benzamidine from Wako Jun-Yaku Kogyo. For heparin, heparin sodium injection (manufactured by Shimizu Seiyaku) was used. A low molecular weight heparin was purchased from Calbiochem, pentosan sulfate, dermatan sulfate (chondroitin sulfate B) and heparan sulfate from Seikagaku Kogyo, pentosan polysulfate and dextran sulfate from Nacalai tesque. Unless otherwise mentioned, the reagents of a special grade were used and culture apparatus were purchased from Becton Dickinson and Co. Human serum albumin (HSA) used was manufactured by Juridical Foundation the Chemo-Sero-Therapeutic Research Institute.

(2) Measurement of TFPI activity

An inhibitory activity on Factor Xa formation by TF/Factor VIIa complex was measured by using a synthetic substrate and an inhibitory activity of heated normal human plasma was set as 1 U/mL [Sandset, P. M., Thromb. Res., 47, p389 (1987)].

(3) Preparation of antibody (A) $TFPI_{265-276}$-PAb (anti-human $TFPI_{265-276}$ antibody):

A synthetic peptide of the C-terminal region ($Lys^{265}$-$Met^{276}$) was prepared and used for immunization of rabbit by a known method to give an antiserum. From this antiserum, an IgG fraction was obtained by a chromatography using a Protein A column (Biorad; Affigel protein A) and then only a specific polyclonal antibody was purified by an affinity chromatography using Sepharose 4B to which the synthetic peptide was bound (the synthetic peptide was bound to CNBr-activated Sepharose 4B (Pharmacia) in accordance with the specifications).

(B) TFPI-MAb (anti-human recombinant TFPI monoclonal antibody);

The recombinant TFPI expressed from CHO cells was prepared in accordance with Nordfang et al. [Nordfang, O., Biochem., 30, p10371 (1991)] and was used as an antigen for immunization of mouse, followed by the known procedure to give TFPI-MAb.

(3) Intact ELISA

A sandwich ELISA was constructed using TFPI-MAb as a primary antibody and $TFPI_{265-276}$-PAb as a secondary antibody. Only the intact TFPI can be measured by this ELISA.

(4) Intact percent

The measurement of the TFPI activity shows results of both of the cleaved TFPI and the intact TFPI whereas the intact ELISA shows results of only the intact TFPI. Accordingly, a ratio of values from the intact ELISA to values from the measurement of the TFPI activity (C-terminal antigen/activity) was used as an intact percent for an indicator of a rate of the intact TFPI.

Example 1 (Expression of recombinant TFPI)

Example 1-1 (Amplification of TFPI cDNA)

Using human placental CDNA library λgt11 (Clonetech) which is diluted by 10 folds with sterilized water and treated at 100° C. for 2 minutes as a template and 5' and 3' end synthetic oligonucleotides having a nucleotide sequence determined based on the sequence reported by Wun et al. [Wun, T C., J. Biol. Chem., 263, p6001 (1988)] as primers, cDNA of TFPI was amplified by Polymerase Chain Reaction (PCR) with 30 cycles of 94° C. for 1 min., 50° C. for 1 min. and 72° C. for 4 min.

The primers used had the following nucleotide sequences. The obtained PCR products were subcloned and then nucleotide sequences thereof were confirmed by the dideoxy method.

5'-CTC GAG ATG ATT TAC ACA ATG AAG AAA GTA-3' SEQ ID NO:1

5'-GGA TCC TTA GTA GAA TTA ATG TTA CAT TGC-3' SEQ ID NO:2

Example 1-2 (Construction of plasmid expressing TFPI in animal cell and production of cells expressing recombinant TFPI)

The expression plasmid, pCAG.TFPI.dhfr was constructed as follows. The cDNA obtained in Example 1-1 was inserted into the expression vector pCAG.dhfr that contains the chicken β-actin promotor and a dihydrofolate reductase expression unit [Japanese Patent First Publication (Kokai) No. 268968/1993, FIG. 9].

Chinese hamster ovary cells (CHO cells) deficient in dihydroforate reductase (dhfr), DG44 [Urlaub, G., Somatic cell and Molecular Genetics, 12, p555 (1986)], were inoculated onto a 6-well plate at $2 \times 10^5$ cells/well and were cultured in 3 mL MEM alpha medium containing 10% fetal bovine serum (hereinafter referred to as "FBS")/well at 37° C. overnight. The cells were transformed with the expression plasmid pCAG.TFPI.dhfr by the lipofectin method. The method and reagent for lipofectin method were followed to the description of the Kit manufactured by BRL. After culture for 16 hours, the culture medium was exchanged with 3 mL/well of MEM alpha containing 10% dialyzed FBS and no nucleoside (hereinafter referred to as "selection medium"), and thereafter, the culture was continued while the selection medium was exchanged with a fresh selection medium for every three to four days. As a result, only dhfr(+) cells with introduction of pCAG.TFPI.dhfr survived. About one month after the transformation, the selection medium was exchanged with a fresh selection medium and the expressed activity per day was calculated. As a result, cells expressing the recombinant TFPI at about 1.5 to 2 U/day/$10^6$ cells were obtained. The expressed activity was calculated by inoculating the transformed cells onto a 6-well plate at $1 \times 10^6$ cells/well, exchanging the culture medium with a selection culture medium containing a final concentration of 1 mM butyrate the next day, and measuring the cell count and the activity after 24 hours.

The cells obtained above were cultured in a selection medium supplemented with a final concentration of 5 nM methotrexate (hereinafter referred to as "MTX") in order to amplify the TFPI gene. The culture was continued for about 3 weeks while the culture medium was exchanged with a fresh selection medium with every 3 to 4 days. Then, the cells were cultured in a selection medium containing a final concentration of 10 nM MTX, and thereafter, the culture was further continued with stepwise increase of MTX concentration up to 80 nM to conduct the gene amplification. In order to obtain cells which can stably express the recombinant TFPI even under conditions with no nucleic acid pressure, the cells which acquired resistance against 80 nM MTX were cloned by a limiting dilution method as follows. The cells in a logarithmic growth phase were harvested and supplemented with MEM alpha/10% FBS medium (with no MTX), were inoculated onto a 96-well plate (Nunc) at 0.5 to 1.0 cell/well, and were cultured in the same culture medium. After about a week, cell colonies of a monoclonal clone appeared and were expanded to a 24-well plate. At the logarithmic growth phase, the culture medium was exchanged with a fresh medium and the TFPI activity of a culture supernatant in each clone was measured after 24 hours. Based on this measurement, 10 clones with higher TFPI activity were selected, were further expanded to a 6-well plate and the expressed activity per cell was measured. As a result of this screening, cells expressing the recombinant TFPI at 11 to 14 U/$10^6$ cells/day (CHO-TFPI No. 7) were obtained.

Example 2 (Protective effect of heparin from cleavage of expressed intact recombinant TFPI)

Figure 1:
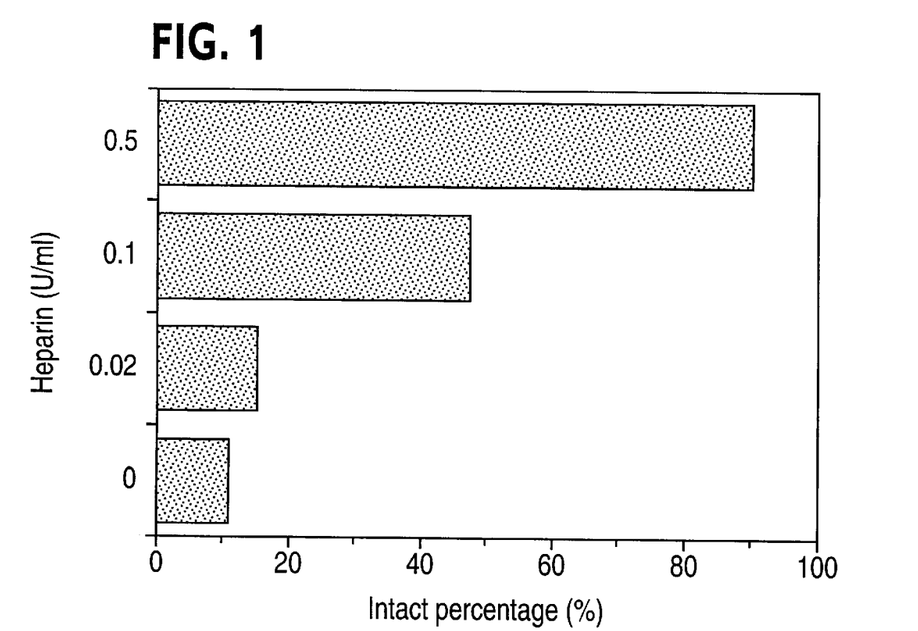
FIG. 1 shows a protective effect of heparin added in a culture medium of CHO cells expressing the recombinant TFPI from cleavage by proteases as an intact percentage, as conducted in Example 2. Heparin was added to a base medium, ASF culture medium 104—0.5% HSA, at various concentrations (0.02 to 0.5 U/mL).

CHO-TFPI No. 7 obtained in Example 1 was inoculated onto a 6-well plate at $2 \times 10^6$/well and was cultured at 37° C. The next day, the culture medium was exchanged with a serum free culture medium (ASF medium 104—0.5% HSA; 3 mL) supplemented with various concentrations of heparin and the culture was further continued. After 24 hours, an amount of the intact TFPI in the culture medium was measured. As shown in FIG. 1, the intact percentage was around 10% in case of the heparin free culture medium whereas the protecting effect of heparin was proved in case of the culture medium supplemented with heparin at 0.1 U/mL or more. In addition, the percentage of the intact TFPI was about 90% when heparin was added at 0.5 U/mL.

Example 3 (Purification of recombinant TFPI from culture supernatant of TFPI-expressing cell)

The clone obtained in Example 1-2, CHO-TFPI No. 7, was expanded stepwise, was finally inoculated into Cell Factory (6000 cm², Nunc) and was cultured in 1 L ASF culture medium 104 containing 0.5 U/mL heparin and 0.5% HSA in the presence of 5% $CO_2$ at 37° C. The Cell Factory was operated continuously while the culture medium was exchanged with a fresh culture medium for every 1 to 2 days, and 10 L of the culture medium containing the recombinant TFPI was finally obtained. Using this material, the recombinant TFPI was purified by the following procedure. To the collected culture supernatant were added a final concentration of 10 mM HEPES (pH 7.2), 0.5 mM p-APMSF and 10 mM benzamidine, and the mixture was filtered through 0.45 μm membrane filter (Millipore) and then concentrated to about 1/10 fold with a hollow fiber membrane (HIP30-20; Amicon). The concentrate was applied onto MAb-Sepharose, wherein MAb was coupled to CNB-ractivated Sepharose 4B (Pharmacia) in accordance with the specifications, equilibrated with TBS (50 mM Tris-HCl (pH 7.5), 0.1 M NaCl). After thorough washing with TBS, elution with 0.2 M Glycine (pH 2.3) gave an almost unique peak. The eluted fraction was immediately neutralized with 1 M Tris.

Figure 2:
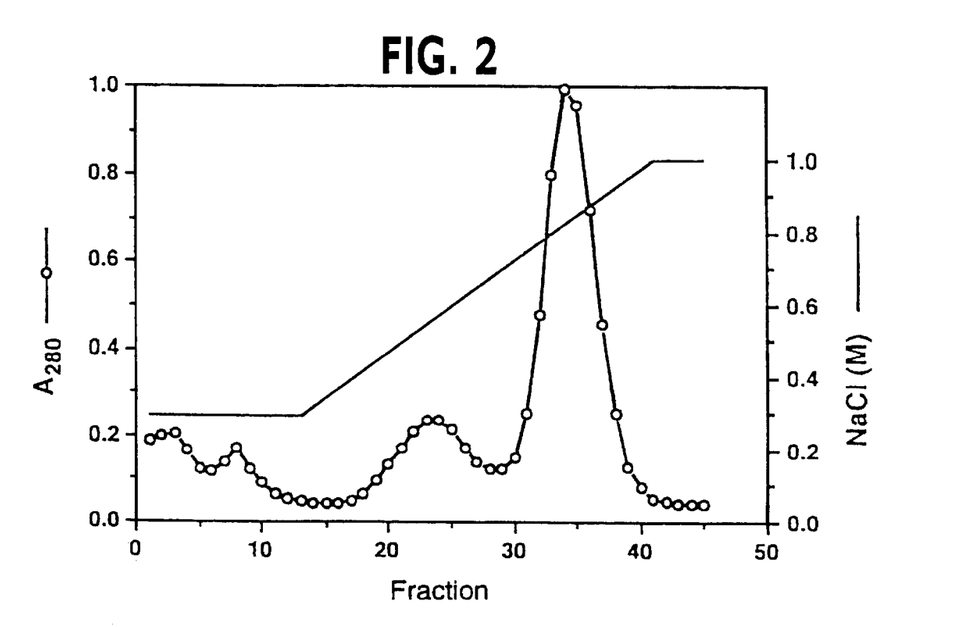
FIG. 2 shows an elution pattern of heparin Sepharose chromatography to which a culture medium obtained by culturing the recombinant TFPI-expressing CHO cells in Cell Factory was applied, as conducted in Example 3.

The fraction containing TFPI was pooled, was diluted with an equilibrated buffer (20 mM sodium citrate (pH 7.0), 0.3 M NaCl) to 3 folds and then the diluted fraction was applied onto a heparin Sepharose (Pharmacia) equilibrated with the same buffer. After washing with a 10-folds amount to the gel volume of the same buffer, elution with a linear gradient up to 1 M NaCl gave two peaks of the TFPI activity. The first peak was eluted with about 0.5 M NaCl and accounted for about 20% with absorbance at 280 nm. The second peak was eluted with about 0.8 M NaCl and almost all of absorbance was found in this peak (see FIG. 2). Flow rate; 15 mL/cm²/hr, gradient; 75 mL, and fraction; each 2.5 mL.

These peaks were pooled and resolved by SDS-PAGE under reducing condition, then visualized by Coomassie brilliant blue staining. As a result, the first peak fraction was of about 42 kD whereas the second peak fraction was of about 45 kD. Western Blotting of these fractions revealed that both peak fractions reacted with TFPI-MAb but the first peak fraction did not react with $TFPI_{265-276}$-PAb.

The C-terminal of TFPI in each fraction was identified by the following procedure. About 130 μg of TFPI from each fraction was dissolved in 500 μL of Tris-HCl (pH 8.4), 6M guanidine hydrochloride, 10 mM EDTA and 350 μg of DTT and then TFPI was reduced by being left to stand at 50° C. for 2 hours. To the mixture was added 2 μL of 4-vinylpyridine (Aldrich Chemical) and the mixture was left to stand at room temperature for 1.5 hours to give a reduced pyridylethylated TFPI, which was then dialyzed against 10 L of ammonium bicarbonate solution and lyophilized. The obtained pyridylethylated TFPI (40 μg) was dissolved in final 100 μL of 50 mM Tris-HCl (pH 9.0) and 4 M Urea. Lysylendopeptidase (1 μg; manufactured by Wako Jun-yaku Kogyo) was added to the solution and the pyridylethylated TFPI was digested at 37° C. for 2.5 hours. The obtained digested products were developed by HPLC under the following conditions. μBondasphere C18 column (Waters; 2.1×150 mm) was developed with 8 mL gradient of from 0.05% TFA to 0.05% TFA+40% acetonitrile at a flow rate of 0.2 mL/min. and then eluted with 2 mL gradient up to 0.05% TFA+80% acetonitrile. The obtained peptide fractions were analyzed by the Edman degradation method to determine an amino acid sequence. As a result, $I^{266}$–$K^{274}$ corresponding to the C-terminal region was confirmed from the second peak fraction. On the other hand, the corresponding peptide fraction could not obtain from the first peak fraction and an amino acid sequence up to $K^{249}$ was confirmed. These results show that the first peak fraction contains a molecular species where the C-terminal region up to $K^{249}$ was cleaved whereas the second peak fraction corresponds to the intact TFPI.

Example 4 (Medium scale production with roller bottle)

The intact TFPI is not always subjected to a constant amount of protease during the culture period. Although this situation can be dealt with by controlling an amount of heparin to be added to a culture medium, a cleavage rate of the intact TFPI may be variable from the early stage to the late stage of culture. In order to further clarify the effect of heparin, a long term culture was conducted with a Roller Bottle (manufactured by Coning; 28280 BT 1700). CHO-TFPI No. 7 was expanded stepwise and was finally inoculated in ASF medium 104—5% FBS in Roller Bottle at 1×10⁸ cells per bottle. Four days after the inoculation, the culture medium was exchanged with a serum free medium (ASF 104—0.5% HSA—0.5 U/mL heparin—1 mM butyrate). This day was counted as the first day of culture and the culture was further continued for 24 days. On and after the 4th day of culture, the culture medium was exchanged with a fresh medium for every two days and a collected culture supernatant was purified as described in Example 3.

Figure 3:
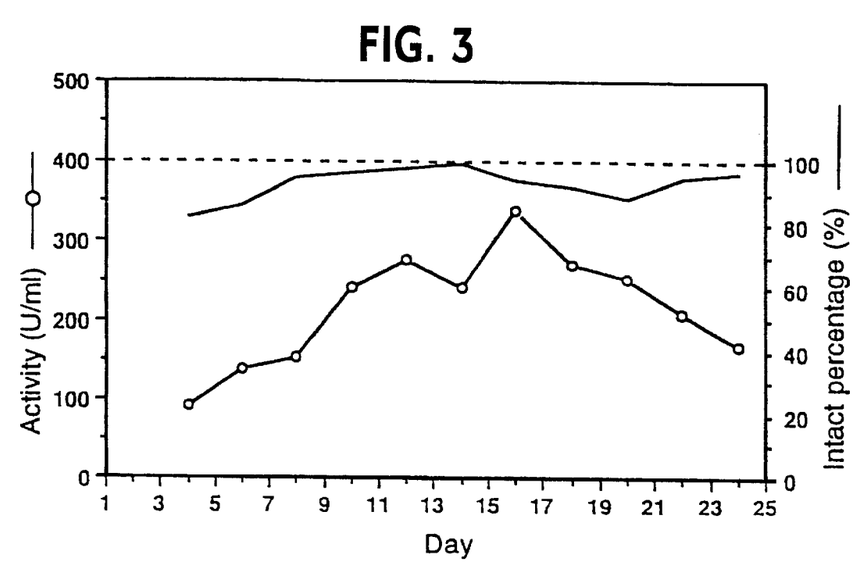
FIG. 3 shows a change in the expressed activity and the intact percentage with passage of time in a roller bottle culture, as conducted in Example 4. On and after the 4th day, a culture medium was exchanged with a fresh medium every two days and the expressed activity and the intact percentage were measured.
Figure 4:
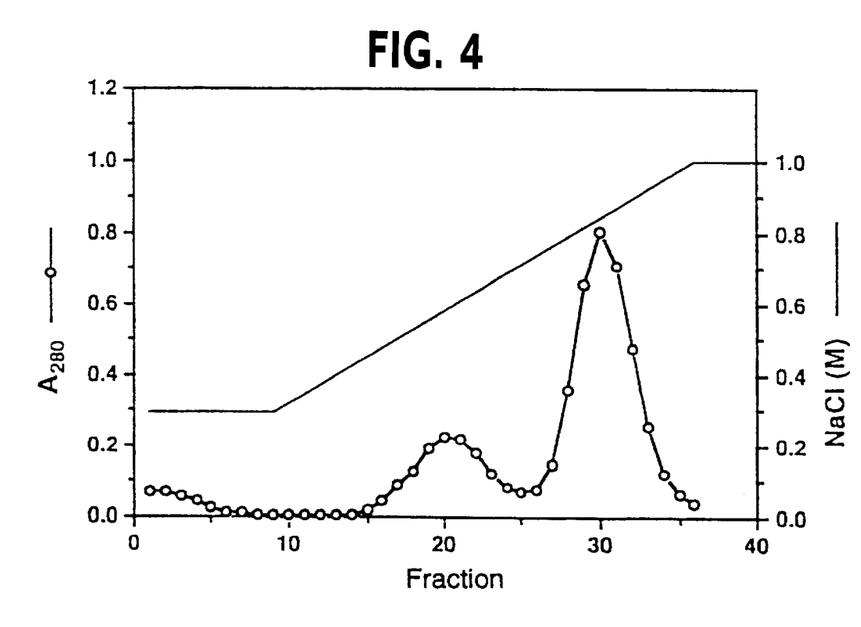
FIG. 4 shows an elution pattern of heparin Sepharose chromatography to which a culture supernatant obtained at an early stage (6th day) of the roller bottle culture was applied, as conducted in Example 4.
Figure 5:
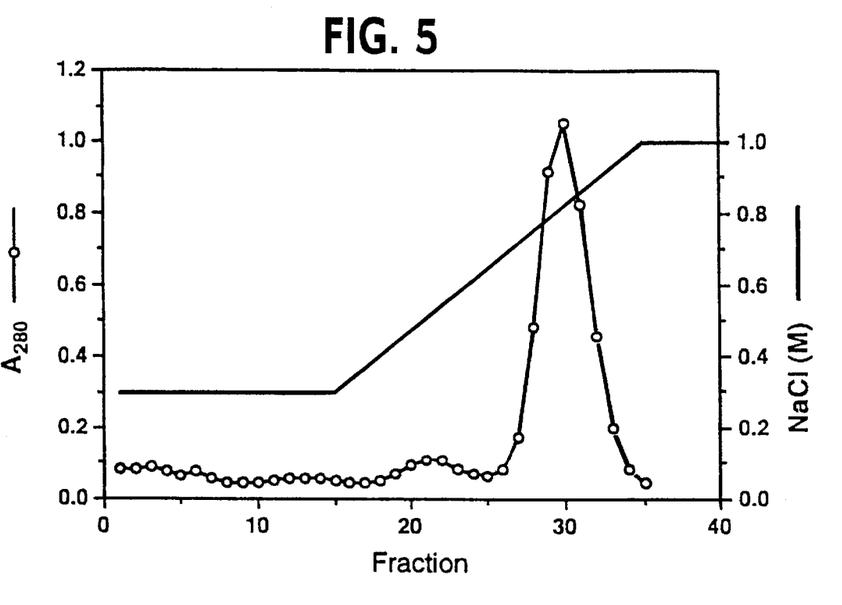
FIG. 5 shows an elution pattern of heparin sepharose chromatography to which a culture supernatant obtained at a late stage (22nd day) of the roller bottle culture was applied, as conducted in Example 4.

The results are shown as a change in the expressed activity and the intact percentage (FIG. 3), and as a developing pattern of heparin affinity chromatography after purification [FIG. 4: early stage of culture (6th day), FIG. 5: late stage of culture (22nd day)]. As shown in FIGS. 3 to 5, the intact TFPI has been protected at a high rate till the late stage of culture and 80% or more of the finally purified TFPI was collected as the intact TFPI from the developing pattern of heparin Sepharose chromatography. Accordingly, the protecting effect of heparin against cleavage of the intact TFPI was stably exhibited even in a relatively long term culture.

The above results proved that the intact TFPI can be protected from protease cleavage in culture by culturing the transformed cells in a culture medium supplemented with heparin and hence the intact TFPI can be collected at a high rate. Next, in order to confirm that the same effect of heparin of the present invention can be found in a host cell of another cell strains and another homologous substances (sulfated polysaccharides) other than heparin also exhibit the protecting effect like heparin, the following experiment was conducted.

Example 5 (Protecting effect of sulfated polysaccharides against cleavage of intact TFPI with culture supernatant from various cell strains)

As mentioned above, only cleaved TFPI can be prepared from a culture supernatant of transformed cells expressing the recombinant TFPI, and hence, it is assumed that the expressed TFPI is subjected to cleavage by protease derived from the host cell. In this respect, the intact TFPI was added to a culture supernatant of various host cells and the culture supernatant was kept at 37° C. overnight in the presence of a sulfated polysaccharide, and thereafter, the protecting effect of the sulfated polysaccharide was examined.

Example 5-1 (Protecting effect of heparin against cleavage by host cell-derived protease)

Figure 6:
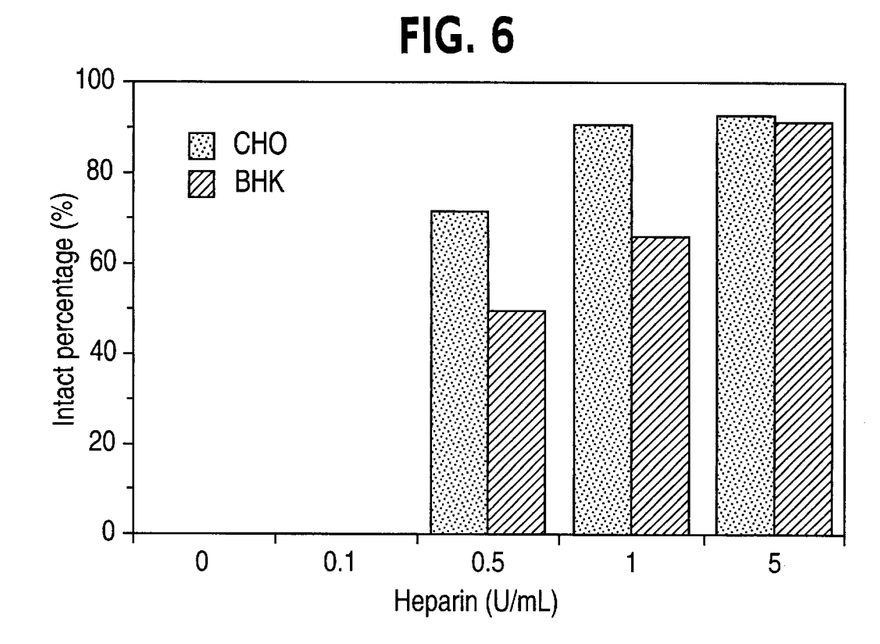
FIG. 6 shows a protective effect of heparin from cleavage of the intact TFPI by culture supernatants of various culture cells, as conducted in Example 5-1.

A culture medium supplemented with a host cell-derived protease was prepared by the following procedure. Among culture cell strains generally used as a host cell, CHO cells and BHK cells inoculated in MEM-alpha medium supplemented with 10% FBS were cultured in a usual manner. The culture was continued until the cultured cells become almost confluent and, after washing the cells with PBS, the culture medium was then exchanged with a serum free medium (ASF104). After the culture was continued for additional 2 to 3 days and the condition of the cells became slightly worsened, the culture solution was collected. The culture solution was subjected to centrifugation to separate floating cells, which were used in the following experiment. Firstly, to each of the culture supernatants were added the intact TFPI (final concentration; 2.3 μg/mL), HSA (final concentration; 0.5%) and heparin (final concentration; 0 to 5 U/mL), and then the mixture was incubated at 37° C. overnight. A percentage of the intact TFPI in these samples were evaluated by the intact ELISA by setting the percentage before incubation as 100%. As a result, as shown in FIG. 6, the protecting effect of heparin was confirmed against cleavage by a protease derived from any host cell at a final concentration of 0.5 U/mL or more of heparin. Using the culture supernatant of BHK cells which showed a strong protease activity, the following Experiment was conducted.

Example 5-2 (Protecting effect of various sulfated polysaccharides against protease cleavage of intact TFPI).

Figure 7:
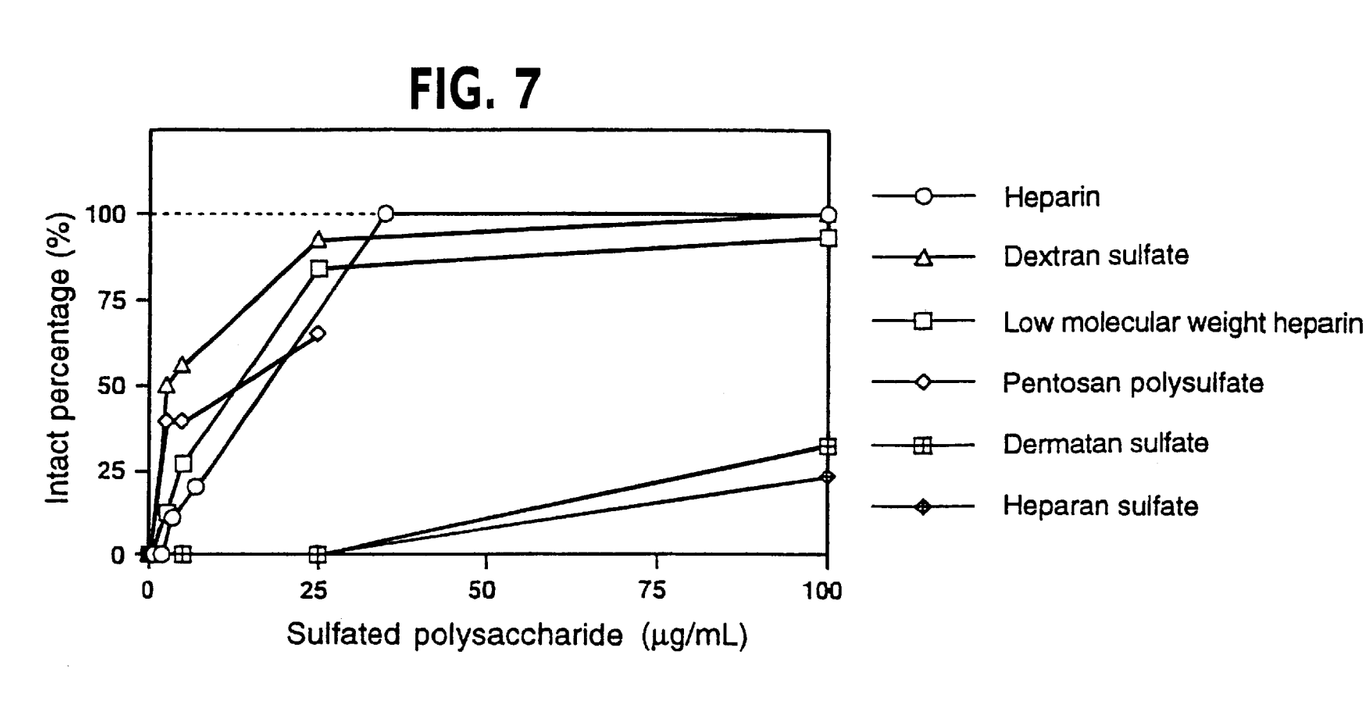
FIG. 7 shows a protective effect of various sulfated polysaccharides from cleavage of the intact TFPI, as conducted in Example 5-2.

The sulfated polysaccharides tested include heparin, a low molecular weight heparin, pentosan polysulfate, dermatan sulfate, dextran sulfate and heparan sulfate. To the culture supernatant of BHK cells were added the intact TFPI at a final concentration of 6.9 μg/mL and various sulfated polysaccharides at a final concentration of 0 to 100 μg/mL and the culture supernatant was incubated at 37° C. overnight. A specific activity of heparin was calculated as 140 U/mg. As in Example 5-1, the cleavage percentage was evaluated before and after the incubation by the intact ELISA, and as a result, all of the sulfated polysaccharides tested, though to a varied extent, proved to show the protecting effect against protease cleavage of the intact TFPI as shown in FIG. 7. The protecting effect was highest in heparin, dextran sulfate and a low molecular weight heparin. Pentosan polysulfate also showed a high protecting effect. In case of dermatan sulfate and heparan sulfate, the effect was confirmed at a higher concentration.

As is clear from the above-mentioned results, it was proved that the protecting effect of heparin is also effectively shown in case of other cell strains and that other sulfated polysaccharides other than heparin also exhibit the same protecting effect like heparin.

As shown above, in the attempt to obtain the intact TFPI through expression of the recombinant TFPI in an animal cell, the intact TFPI can be firstly obtained by the present invention in an amount sufficient for industrial scale by adding a suitable amount of the sulfated polysaccharide in accordance with present invention even when those cell strains from which the intact TFPI has hitherto hardly been obtained were used as a host cell. The advantage of the present invention will be clearly understood when compared with reports by researchers other than the present inventors [Wun, T C., Thromb. Haemost., 68, p54 (1992); Nordfang, O., Biochem., 30, p10371 (1991)].

What is claimed is:

1. In a process for preparing Tissue Factor Pathway Inhibitor (TFPI) by the genetically engineered technique by the use of a transformed animal cell wherein a DNA encoding human TFPI is introduced, the improvement which comprises culturing said transformed animal cell in a culture medium supplemented with a sulfated polysaccharide to protect an intact TFPI produced by said transformed animal cell from cleavage by proteases present in the culture medium.

2. The process of claim 1 wherein said sulfated polysaccharide is selected from the group consisting of heparin, a low molecular weight heparin, pentosan polysulfate, dextran sulfate, heparan sulfate, and dermatan sulfate.

3. The process of claim 2 wherein said sulfated polysaccharide is heparin.

4. The process of claim 1 wherein said transformed animal cell is a chinese hamster ovary (CHO) cell or a hamster kidney (BHK) cell.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (xi) SEQUENCE DESCRIPTION: SEQ ID NO:1:

CTCGAGATGA TTTACACAAT GAAGAAAGTA      30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (xi) SEQUENCE DESCRIPTION: SEQ ID NO:2:

GGATCCTTAG TAGAATTAAT GTTACATTGC      30